United States Patent [19]

Kraus

[11] 4,306,564

[45] Dec. 22, 1981

[54] ELECTRIFICATION ATTACHMENT FOR AN OSTEO-SYNTHESIS IMPLANTATE

[76] Inventor: Werner Kraus, Kaulbachstrasse 71, D-8000 München 22, Fed. Rep. of Germany

[21] Appl. No.: 944,917

[22] Filed: Sep. 25, 1978

[30] Foreign Application Priority Data

Sep. 22, 1977 [DE] Fed. Rep. of Germany ....... 2742741

[51] Int. Cl.³ .............................................. A61N 1/18
[52] U.S. Cl. ................................ 128/419 F; 128/784
[58] Field of Search .................. 128/419 F, 82.1, 783, 128/784, 785, 799

[56] References Cited

U.S. PATENT DOCUMENTS

| | | | |
|---|---|---|---|
| 3,650,276 | 3/1972 | Burghele et al. | 128/784 X |
| 3,783,880 | 1/1974 | Kraus | 128/82.1 |
| 3,820,534 | 6/1974 | Kraus et al. | 128/82.1 |
| 3,890,953 | 6/1975 | Kraus et al. | 128/419 F X |
| 3,915,151 | 10/1975 | Kraus | 128/419 F X |

Primary Examiner—Lee S. Cohen
Attorney, Agent, or Firm—Frishauf, Holtz, Goodman & Woodward

[57] ABSTRACT

To permit electric stimulation of tissue and specifically bone tissue to which an osteosynthesis plate or a bone nail has been attached, and provide electrical energy by induction from an external induction coil, a support body 22, 110, 222 is provided for attaching association with the osteosynthesis implantate; at least one induction coil 24, 118, 224 is embedded in, or secured to the body, electrodes 28, 36, 80, 118a, 228, 236 are connected to the windings of the coil, one of which is connectable with a conductive portion of the osteosynthesis implantate, the other electrode being exposed to bone tissue or soft tissue of the patient. When used in association with a hollow, slotted bone nail FIGS. 1 to 6, 12 to 24), the implantate can be constructed as an elongated plastic rod which can be introduced into the bone nail, one electrode protruding therefrom and making contact with the bone nail, the rod being of plastic which can be cut to length to fit the length of the bone nail; when the implantate is a plate (FIGS. 9 to 11), the windings can be included in a strip arranged for slipping on and clamping around the edge of the plate, with projecting electrode connections.

18 Claims, 26 Drawing Figures

ELECTRIFICATION ATTACHMENT FOR AN OSTEO-SYNTHESIS IMPLANTATE

Reference to related publications:
U.S. Pat. No. 3,745,995 (corresponding: German Pat. No. 19 18 229)
U.S. Pat. No. 3,820,534 (corresponding: Swiss Pat. No. 551,201)
U.S. Pat. No. 3,918,440
German Disclosure Document DE-OS No. 23 11 817

The present invention relates to a surgical prosthesis, and more particularly to an osteosynthesis implantate, which, after its manufacture, can be associated with an electrical pick-up element to provide a small electrical voltage across the implantate and surrounding tissue of the patient to stimulate healing processes.

The term "tissue" as used herein includes soft tissue as well as bone tissue, unless it clearly appears otherwise.

BACKGROUND AND PRIOR ART

It has previously been proposed—see the referenced U.S. Pat. Nos. 3,745,995 and 3,820,534—to provide an inductive receiving coil, preferably having a ferromagnetic core, for association with osteosynthesis implantates. The receiving coil has two or more connecting terminals, connected to electrodes which are attached to an injured or damaged bone which is fixed in relative position by the osteosynthesis implantate. Such an implantate may, for example, be a bone nail, securing together the ends of a fractured bone by extending through the marrow duct. After the operation of introducing the bone nail, and of closing the wound, a low-frequency electrical current is induced in the coil which flows through the electrodes and the damaged bone region, and promotes healing and reformation of bone substance.

Such osteosynthesis implantates are known as electro-osteosynthesis implantates and are provided with the receiving coil and the electrode connections, as delivered from the manufacturer. The manufacture of any one electro-osteosynthesis implantate requires individual, special manufacture in which the electrical winding elements and the osteosynthesis implantate are individually associated. Such implantates may, also, be in the form of flat or bendable plates. The winding section is individually and securely connected to the implantate by adhesion, clamping connection or welding; likewise, the electrodes or electrode connection are so adhered or connected. Surgical clinics, trauma stations in hospitals, and the like, require a large stock of different types of electro-osteosynthesis implantates, for example bone nails of many different lengths in many different diameters. Such electro-osteosynthesis implantates are expensive and stocking and storage of a large number of such items in many different sizes, the requirements for which are hardly predictable, is a substantial drain on limited financial resources of public and private health facilities. Frequently, therefore, the patient is subjected to multiple surgical procedures since electro-osteosynthesis implantates were frequently introduced into the patients only in a second operation, after the initial operation of fixation of the bone has taken place, the type and size of the required electro-synthesis implantate has been determined and the appropriate unit has been ordered and received from the manufacturer.

Developments in surgical devices have been undertaken to reduce the financial load on health facilities and to reduce the requirement for stocking of specific electro-implantates. U.S. Pat. No. 3,820,534 describes a belt-like element which is furnished with electrodes and a connecting element on which a coil is secured. After implantation of a bone nail, for example, the belt-like element is placed around the bone, and the connecting coil can be connected to the bone nail with one terminal. It has also been proposed to provide a loose pick-up coil which is embedded in a biologically tissue-compatible plastic material and which can be connected to bone screws by means of snap-button type connections. The bone screws function as electrodes across which an electric current will flow (see German Disclosure Document DE-OS No. 23 11 817). U.S. Pat. No. 3,918,440 describes such a loose receiving coil in combination with bone screws, in which the head of the bone screws is insulated so that it can be used for attachment of a bone plate. The screws, themselves, form the electrodes which are insulated with respect to the bone plate.

The loosely implanted pick-up coil, as well as the belt-like element, and the snap button or push-button type connections are an entirely satisfactory substitute for premanufactured electro-osteosynthesis implantates. Use of the belt-like element introduces additional complexity; the loose pick-up coil is difficult to secure.

THE INVENTION

It is an object to provide an attachment element for an ordinary osteosynthesis implantate, such as a bone plate, or a bone nail, which can be applied to the implantate so that it can be converted into an electro-implantate during the progress of an operation and which then will be a fully equivalent and effective substitute for a premanufactured electro-implantate.

Briefly, in accordance with the invention, a support body is provided, formed for attaching association with the osteosynthesis implantate. The support body has at least one induction coil therein; when made for association with an osteosynthesis plate, it is formed with means to attach the body to the osteosynthesis plate, for example by a clamp or snap-over connection; if made for association with a bone nail, the body is preferably in elongated rod form of such size and shape that it can be introduced into the hollow portion of the bone nail. At least two electrodes are brought out from the winding within the support body. One of the electrodes, which can be fixedly secured to the end of one of the windings, can be made to be connectable with the osteosynthesis implantate, for example by a bowed spring secured to the body which, when introduced into a bone nail, makes electrical contact therewith. The other electrode can also be secured to the body or otherwise brought out.

The attachment permits the surgeon to fix the bone in standard manner by an osteosynthesis implantate, for example by a plate or by a nail in accordance with standard surgical procedure, and using the ordinarily available implantates. He can then determine whether it would be desirable to have an electrical implantate and, if so, the osteosynthesis plate or the bone nail can be supplied with the attachment in accordance with the present invention and the implantate will then function as an electro-implantate without requiring any further changes or modifications, or a subsequent operation.

A bone nail, which frequently is used, is introduced in accordance with standard surgical procedure, for example by using a trocar, since the electro-attachment is a unit independent of the bone nail and which can be introduced into the longitudinally slotted bone nail after implantation thereof along the slot of the bone nail. The implantate is then operable as an electro-implantate without further procedures. The attachment can be so made that it is universally acceptable by at least a group of bone nails having different internal diameters, as provided by manufacturers, determined, for example, by manufacturing or governmental standards (see, for example, German Industrial Standard DIN 55801).

A standard osteosynthesis implantate, in the form of a bone support plate or in form of a bone nail, and the attachment in accordance with the present invention, together, are substantially simpler and further less expensive than the combined electro-osteosynthesis implantates.

Drawings, illustrating preferred examples, wherein.

Figure 1:
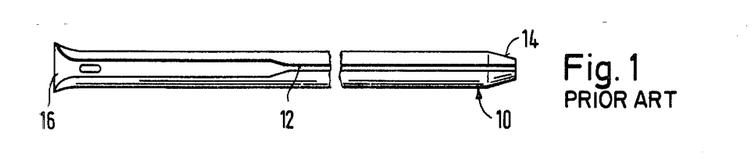
FIG. 1 is a top view of a standard bone nail in accordance with German Industrial Standard DIN 55801, Form B.
Figure 5:
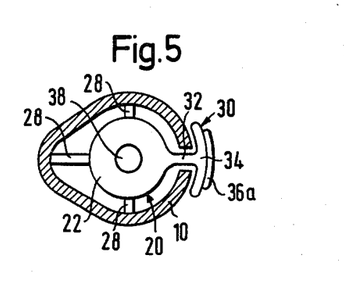
FIG. 5 is a cross section in plane V—V of FIG. 4.

The invention will best be understood when considering first an embodiment for attachment to a standard bone nail, as shown in FIG. 1. The cross section of the bone nail of FIG. 1 is approximately clover leaf-shaped, or pear-shaped (FIG. 5). The bone nail 10 has a longitudinal slot 12, a tapering, somewhat pointed tip 14 and an enlarged terminal end 16.

Figures 2, 3:
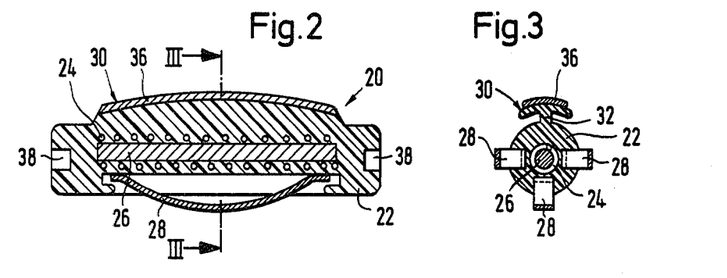
FIG. 2 is a schematic simplified longitudinal section of an electrification attachment for the bone nail of FIG. 1.
FIG. 3 is a cross section in the plane of III—III of FIG. 2.

In accordance with the present invention, the known and conventional bone nail 10 is converted into an electro-bone nail by the attachment 20—see FIGS. 2 and 3. Damaged or diseased or fractured bone tissue is electrodynamically stimulated in the region of injury or disease to stimulate reformation of bone tissue and improve and accelerate the healing process.

The attachment 20, in accordance with the present invention, has a body 22 made of a biologically compatible, tissue-compatible plastic, such as polyethylene, or a carbon-fluoropolymer. A receiving coil 24, shaped like a solenoid, is embedded in the body 22. The receiving coil 24 is only schematically shown in FIGS. 2 and 3, and there illustrated as a single-layer coil; of course, it may be a coil wound of a plurality of tightly arranged windings. The circuit and the electrical terminals have been omitted from the illustration of FIGS. 2 and 3 for simplicity, and will be explained below.

The coil 24 preferably is a cored coil, and has a magnetic core 26 made of a magnetically soft material, having soft-iron characteristics, such as a ferrite, or an iron-nickel alloy. It may also be a permanent-magnet material which, then, preferably, is brought into a partially saturated condition and permits modification of the wave shape of the voltage applied to the electrodes and hence of the currents being supplied to the body tissue.

Embodiment of FIGS. 2 and 3: The body 22 has three leaf-like, spring electrodes 28 secured thereto, for example by being set into a groove of the body (see FIG. 2) which are bowed outwardly. The electrodes 28 are connected together and to one end terminal or end point of the winding 24 and provide electrical connection of the attachment to the metal bone nail 10, by bearing against the inside wall, as illustrated in FIG. 5. The dimensions of the body 22 and the outward bulge of the electrodes 28 are preferably so selected that the same attachment 20 can be used for bone nails of a wide range of diameters, preferably the entire range of diameters of bone nails which are used in surgical procedures. At most, however, two such bodies 20 need be provided, one for a thinner group of bone nails and another for a group of bone nails having a wider diameter. The spring electrodes 28 permit deflection, and hence reliable electrical contact, as well as reliable seating within the bone nail.

The body 22 is formed with an extension 30 which, in cross section, is essentially T-shaped (FIG. 3) and which fits through the slot 12 of the bone nail 10. The upper cross portion 34 of the T-extension 30 (FIG. 5) is bent downwardly so that it fits at least approximately around the curvature of the bone nail 12. Since the body 20, with the integral extension 30, is made of a soft plastic, the pre-bowing of the cross portion 34 can be such that it fits the thinnest nail, since it will then expand, or resiliently bow outwardly to fit over nails or larger diameter. In longitudinal extent, the cross portion 34 can be flat (FIGS. 4, 5) or can be slightly bowed (FIG. 2). An electrode 36 is applied to the outside of the bowed cross extension 34, connected to another point on the winding 24 of the attachment. The electrode 36 is the counter electrode or soft-tissue electrode of the attachment.

Figure 4:
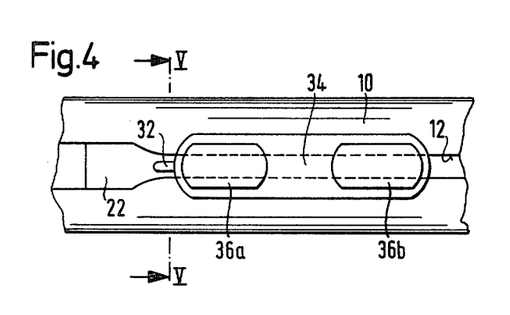
FIG. 4 is a top view of a bone nail of FIG. 1, partly in phantom view.

EMBODIMENT OF FIG. 4

A plurality of separate counter electrodes 36a, 36b can be provided, each one connected to different points on the winding of the coil 24. In all other respects, the structure is similar to that of the embodiment of FIGS. 2 and 3.

The body 22 is preferably formed at its end with recesses, notches or grooves 38 to permit attachment of an insertion or removal tool, and to facilitate insertion or removal of the attachment 20 into or from the nail 10.

In a preferred form, the surgeon is provided, together with the attachment 20, with an additional filler strip which, for example, may be formed similar to an I-beam, that is, have a double T-profile in cross section, and so dimensioned that it cannot pass through the narrow end 14 of the bone nail. The filler strip is then trimmed to the desired length by the surgeon during the operation and introduced into the nail 14 together with the attachment 20 in order to ensure proper spacing of the attachment 20 from the end 14 of the nail, or in order to ensure spacing between a plurality of attachment elements 20 which can be sequentially, axially introduced into the nail 10. The filler strip is preferably made of the same material as that of the body 20, and soft enough so that it can be cut by surgical scissors to the desired length, being supplied, for example, in coil or rod form.

The body 22 with the T-projection 30 and the electrode 36, or the electrodes 36a, 36b, are so dimensioned that they fit within the diameter of the surgical drill with which the opening for the bone nail 10 is drilled.

The entire length of the attachment 20 preferably is between about 3 to 5 cm. The material is somewhat resilient and the dimensions are preferably so arranged that, coupled with the elasticity of the material of the body 22, it is possible to introduce the attachment simply and effortlessly even over a bent-over end formed at the upper end of a bent bone nail and from there into the there widened slot 12. The outer diameter of the attachment is larger than the lower opening of the end 14 of the conically tapering bone nail, so that the attachment device cannot slip upon introduction, or when pulling the nail.

The bone nail 10 is galvanically connected over the electrodes 28 with the coil 24 and forms one of the electrodes, engaging the bone. The other electrode 36, or the electrodes 36a, 36b, may have galvanic, semiconductive or capacitative connection with the adjacent tissue of the patient. If semiconductive or capacitative contact is desired, the electrodes 36 are suitably coated at the outside with either a thin coating of semiconductor material or with a thin coating of an insulator. A galvanic contact is desirable in tissue poorly supplied with blood, or having few blood vessels. In tissue having better blood supply, a semiconductive contact is desirable. This can be obtained by coating the electrode with a thin layer of aluminum oxide ($Al_2O_3$), biological carbon, calcium phosphate, or the like. If the tissue to be contacted has high blood supply, a capacitative contact may be desirable since rise of current beyond the physiologically compatible value of about 100 $\mu$ amperes is prevented. Galvanic contact, due to the high conductivity of tissue well supplied with blood might result in an excessive current flow.

Figure 6A:
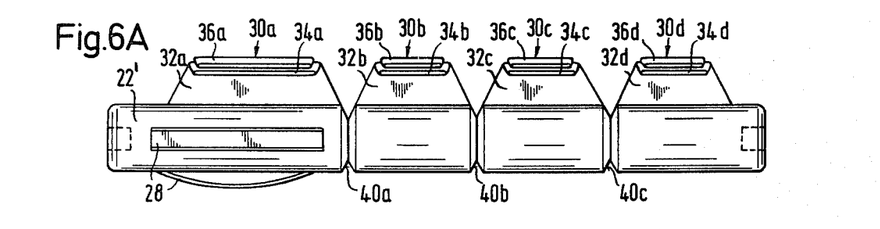
FIG. 6 is a side view of a modified embodiment of the attachment of FIG. 2, in which the electrical circuit inherent in the element is separately shown in view B, and the structural arrangement is shown in view A.
Figure 6B:
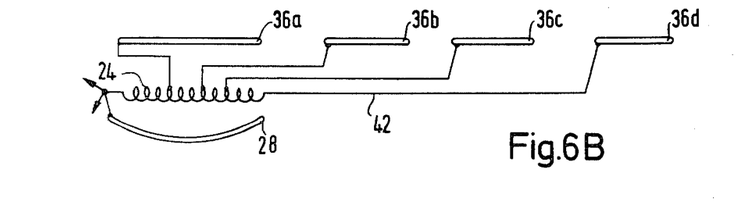

Embodiment of FIG. 6: The attachment has four tissue electrodes 36a, 36b, 36c, 36d. The projection 30 which carries these electrodes is subdivided into four parts 30a, 30b, 30c, 30d (see view (A). The body 22' is constricted between the respective projections, as seen at 40a, 40b, 40c. As seen in the electrical connection of FIG. 6, view B, one end of the coil 24 is connected to the electrode 28 which is used to connect the entire unit to the bone nail 10. The electrodes 28 are identical to those described in connection with FIGS. 2 and 3. The soft-tissue electrodes 36a to 36d are connected to winding terminals of the coil 24 which have increasingly longer distances from the end of the coil 24 connected to the electrodes 28.

The attachment in accordance with FIG. 6 can be fitted to bone nails of any length by cutting or trimming the body 22' at any one of the constrictions 40a, 40b, 40c, which function as break point, so that the extent of contact of the tissue electrodes can be matched to the extent of the region of the fracture which is to be subjected to an electrical current. The soft-tissue electrodes 36b to 36d are connected to the coil 24 by connecting lines 42, for example in the form of thin foils, which can be readily served.

Figure 7:
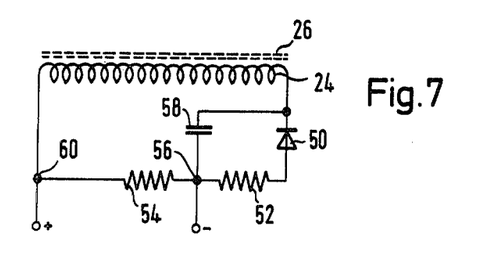
FIGS. 7 and 8 are two schematic electrical diagrams suitable for use in the electrical attachment.
Figure 8:
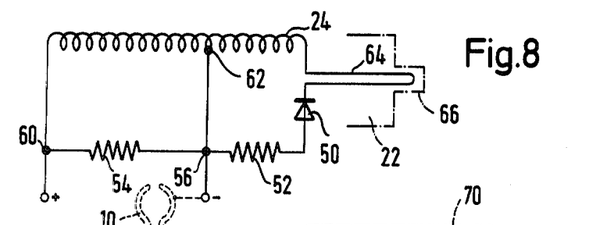

Circuit arrangements, with reference to FIGS. 7 and 8: The circuit of FIG. 7 permits application to the electrodes of a-c with a superimposed d-c. As seen, coil 24 is connected in series with a semiconductor rectifier 50 and two voltage divider resistors 52, 54. The tap point 56 of the voltage divider thus has a d-c potential appear thereat. The magnitude will depend on the a-c induced in the coil 24 and the dimension of the voltage divider resistors 52, 54. The tap 56 is additionally connected by a capacitor 58 to the junction of the diode rectifier 50 and the coil 24 so that the d-c voltage appearing at the tap 56 is superimposed on the a-c supplied by the coil 24. The tap 56 and the terminal 60 of the coil 24 are connected, respectively, to the electrodes 36, 28 (FIGS. 2, 3; 4–6) so that the bone nail is negative with respect to the soft-tissue electrode. The diode 50 preferably is a miniature semiconductor diode with low threshold voltage, for example of 50 mV. The circuit is suitably so dimensioned that the d-c component is about 20% of the peak amplitude of the a-c voltage; in a preferred form, the d-c component is approximately 10% of the peak amplitude of the a-c voltage which may be about 1 V or possibly even higher.

The embodiment of FIG. 8 is a modification of the circuit for an insert in accordance with FIG. 4, in which the a-c is applied to the junction 56 from a tap 62 of the coil 24. The capacitor then need not be used. a-c can be applied to the terminal 56 also over a separate winding, for example formed on another layer of winding 24, and connected between terminals 60 and 56.

The rectifier diode 50 is connected to the winding 24 over a conductor loop which, physically, extends into a projecting portion 66 of the body 22, or 22', respectively, as schematically indicated in broken lines in FIG. 8. If the surgeon decides that no d-c should be applied, he can cut the projection 66 during the surgical procedure, thus interrupting connection between coil 24 and the rectifier diode 50, so that the applied electric current will be only a-c, without a d-c component.

Figure 9:
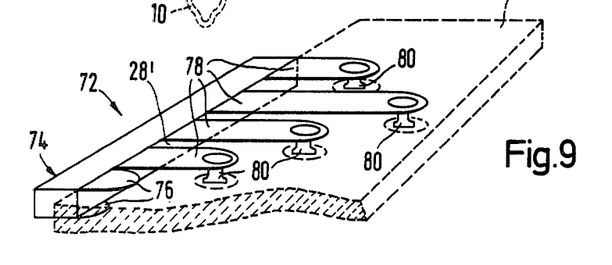
FIG. 9 is a highly schematic perspective view of an osteosynthesis plate, shown in broken lines, to which the electrification attachment in accordance with the present invention has been added.

Embodiment of FIG. 9: The attachment can be used not only with a bone nail, but also with an osteosynthesis plate 70, shown in broken lines in FIG. 9. The attachment 72 has a body 74 made of biologically tissue-compatible material, similar to body 22, in which a receiving coil is located. The receiving coil has been omitted from FIG. 9 for clarity. The body 74 preferably has an approximately rectangular cross section which has a thickness not substantially in excess of that of the plate 70. One or more pairs of knife contact electrodes 76 project from one side of the body 74. Preferably, these contacts 76 are made of springy metal which simultaneously provide electrical connection to the plate 70 as well as ensuring attachment of the body 74 on the plate 70. The electrodes 76, similar to the electrodes 28 of FIGS. 1-6, from electrical contact between the coil in the body 74 and the plate 70. An additional spring electrode 28' may be provided which, similar to the electrodes 28 of the embodiment of FIGS. 2 and 3 is bowed or bulged outwardly and set in at an edge of the body 74, to bear against the edge of plate 70 when the attachment 72 is associated with the plate 70. The body 74 has additional strip-like springy projections 78, made of plastic, and for example molded integrally on the body 74. The projections 78 carry connection arrangements 80, connected over the projections 78 by electrical leads embedded therein with the coil 24 in body 74, similar to the electrodes 36a to 36d, FIG. 6. The connection arrangements 80 permit connection of the coil 74 to bone screws, not shown. The bone screws are insulated with respect to the plate 70 and, simultaneously, form electrodes and attach the plate 70 to the bone. These screws may be constructed as described in the aforementioned U.S. Pat. No. 3,918,440. Projections 78 which are not needed can be trimmed. The projections may have different lengths, as shown, and be so constructed that the location of the connection arrangements 80 corresponds to the position or distribution of the holes in a standard osteosynthesis plate.

Figure 10:
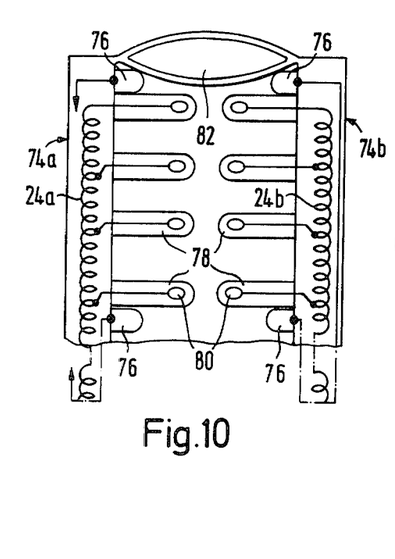
FIG. 10 is a schematic top view of another arrangement of an osteosynthesis plate.

Embodiment of FIG. 10: Two bodies 74a, 74b, each one similar to body 74 (FIG. 9) and each one having a coil 24a, 24b, are located at opposite sides of a plate 70 (not shown, and omitted for clarity). The lower ends of the receiving coils have electrodes 76 and, if desired, electrodes 28 attached thereto, similar to the illustration of FIG. 9, and also omitted from FIG. 10. The sense of winding or connection of the coils 24a, 24b may be the same, or opposite, so that the terminals 80 of facing projections 78 will either carry the same, or different voltage levels. The two bodies 74a, 74b are connected at their ends—only one is shown—by a spring 82 made of plastic material so that the attachment arrangement can be used for plates of different widths.

Figure 11A:
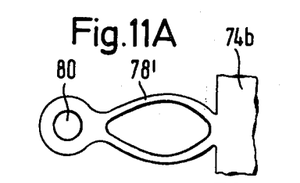
FIG. 11 is a top view of an elastic electrode connection holding arrangement, in which view A illustrates the holding arrangement in relaxed state, and view B the same arrangement in stretched, or stressed state.
Figure 11B:
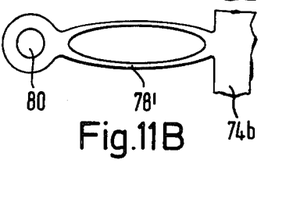

Embodiment of FIG. 11: The projections 78', which carry the connection arrangement 80, are preferably so constructed that they are made of two elastic, oppositely bowed strips, made of plastic. In quiescent state, they are widely bent—see FIG. 11, view A. The strips act like a spring so that the position of the connection arrangement 80 can be matched to different distances of the connection openings between the edge of the plate and the openings for the bone screws themselves, with which the contact elements 80 are to be connected.

Use and application: When using the attachment in accordance with FIGS. 9 and 10, the bone plate 70 is first secured to the bone to be joined, or set. Insulated bone screws having heads which fit the connection arrangement 80 are used at those portions where electrodes are deemed desirable. Thereafter, the attachment body 74, or 74a, 74b, is attached to the plate by sliding it on the longitudinal edge of the plate; the insulated bone screws are then connected with the connection 80 of the projections 78, or 78' (FIG. 11). Those connection elements which are not desired or used are cut off together with the respective projections 78, 78'.

The attachment permits the surgeon to decide during the operation whether healing of a fractured or otherwise injured bone will be promoted by introducing an electrical current to the region of fracture or disease, and if electrodynamic activation of osteosynthesis is desirable.

If the attachment is to be used for an ostesynthesis implantate made of a non-conductive material, such as ceramic, then the electrode which is designed for contact with the implantate is, instead, contacted with a large-area electrode foil, or sheet electrode which, preferably, is in contact with the soft tissue of the patient, preferably with the soft tissue immediately adjacent to the bone which is to heal. When using the embodiment in accordance with FIG. 4 or 5, one of the electrodes 36a, 36b . . . can be used as the tissue counter electrode.

The body 22, or 72, respectively, may also be made of metal and, for example, may include a housing made of a tissue-compatible material such as a cobalt-chrome alloy, chrome-nickel manganese steel; titanium, or the like. The body can then be used directly as the electrode for connection to a metallic osteosynthesis implantate, or as a large-area, soft-tissue electrode. The other electrodes are then suitably insulated from this conductive body, for example by a thin coating of biologically compatible plastic.

Embodiment of FIGS. 12 to 18: A portion of at least one winding of the receiving coil is brought out from the electrically insulating surrounding or housing made of tissue-compatible material and is so located at the surface of the housing or embedding material that the portion of the winding forms the electrode for the tissue which surrounds the osteosynthesis implantate with which the attachment is associated.

In this embodiment, at least one tissue electrode is formed directly by a portion of the winding of the receiving coil. The receiving coil, suitably, is a single-layer winding having a strip or ribbon-like conductor and effectively each turn of the winding can have a portion active as a tissue electrode. The winding, preferably, is connected at a fixed point, for example in the center, but preferably at an end, with the osteosynthesis implantate. The osteosynthesis implantate is made of metal, or is coated with a surface metal coating, so that the implantate additionally acts as an electrode.

Figures 14, 17, 18:
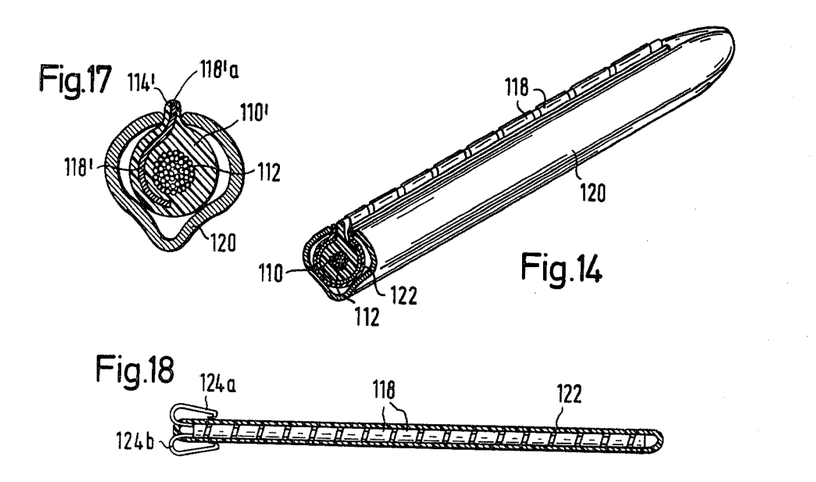
FIG. 14 is a schematic perspective view, partly in section, of the bone nail of FIG. 1 with the attachment of FIG. 12 introduced therein.
FIG. 17 is a transverse cross section of the embodiment of FIG. 15 taken in the inclined plane XVII—XVII of FIG. 16.
FIG. 18 is a side view of another embodiment of the invention generally shown in FIGS. 12 to 15.
Figure 15:
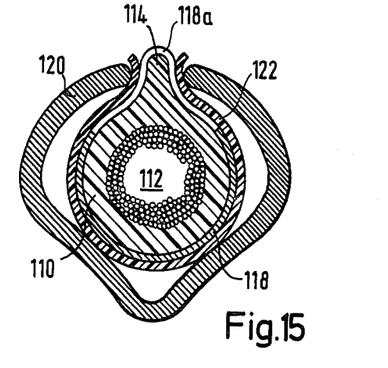
FIG. 15 is an enlarged cross-sectional schematic view taken in the plane of XV—XV of FIG. 12.

Basic structure, FIGS. 12 to 15: An elongated rod-like body 110, made of a flexible, tissue-compatible insulating material like PTFE, preferably includes a magnetic core 112 (FIG. 15) made of highly permeable, magnetically soft material such as mu metal, or permalloy. The body 10 should be flexible so that it can be introduced into bent bone nails and, therefore, the core preferably is made of a bundle of wires of the respective ferromagnetic material, as best seen in FIG. 15. The body 110 has a longitudinal ridge 114, projecting from the remainder which, essentially, is circular. The ridge 114 is rounded so that the overall cross section of the body is approximately pear-shaped—see FIG. 15. The body 110 has a spiral winding 118 placed thereon made of a ribbon or strip-like conductor which fits and matches the surface of the body 110. The strip-like conductor is made of a biologically compatible material at least in those portions at which it is exposed since it will come in contact with tissue or body fluids. Preferably, the strip-like conductor is made of osteosynthesis metal, such as a cobalt-chrome molybdenum alloy, known under the trade name "Vitallium".

The length of the body 110 can be in the order of about 25 cm. The strip-like conductor can be about 3 to 6 mm wide and about 0.1 mm thick. 10 to 50 winding loops can be placed on this body.

In a practical embodiment, the winding 118 was made of an osteosynthesis metal in accordance with German industrial specification 4401, 5 mm wide and 0.1 mm thick, with 32 windings. The distance between the edges of adjacent windings was about 0.8 mm. The terminal ends of the windings are secured to the body 110, for example by embedding them in the body, by a screw, or the like.

The cross-sectional dimension of the body 110, supplied with the winding 118 is so selected that the body and the winding and a foil cover 122 (FIG. 15) can be easily introduced into the upper opening of a bone nail, by slipping it axially therein, and provide a good fitting seat therein.

The insulating foil 122 consists of a foil of tissue-compatible plastic and is provided to insulate the winding 118 at least over the largest portion of its length with respect to the metallic nail 120. The foil 122 can be omitted if the nail is made of an insulating material, or if insulation is otherwise ensured. If the nail is of metal, a foil of 0.1 mm thick PTFE has been found eminently suitable. The foil 122 can be attached to the end of the body 110 which is first introduced into the nail, or may be formed with a closed end, similar to a cap, in order to prevent change of position of the foil 122 with respect to the body 110 upon introduction of the foil-body combination into the nail.

The winding 118 can be entirely insulated against the nail 120. In a preferred form, however, one point, for example in the center, or preferably at the end which is last introduced into the nail is electrically connected with the nail 120, if the nail 120 is made of metal. The winding 118 is then formed with a loop end 124 (FIGS. 12, 13) which also forms a terminal connection. The loop end 124 is not coated by the foil 122 and engages the inner wall of the nail after introduction into the nail 120.

After implantation, a low-frequency a-c voltage is induced in the winding 118. A suitable frequency is, for example, somewhat under 30 Hz, as known, and standard in connection with electro-implantates, and described in the reference literature. Magnetic field strengths in the order of about $10^{-2}$ Tesla permit induction in the winding 118 of a-c voltages in the order of several hundred milli volts. The low-frequency a-c voltage becomes effective between the free portions 118a (FIGS. 12, 15) of the winding 118, acting as soft-tissue electrodes, and stimulates growth of the adjacent bone tissue, as known. The resistance of the winding 118, preferably, is low, specifically below 30 ohms and preferably below 10 ohms, which can be readily ensured by the large cross section of the strip or ribbon-like conductor forming the winding 118. The electrical shunt or parallel circuit through the tissue which is adjacent to the winding portions 118a can then be neglected for all practical purposes.

Figure 12:
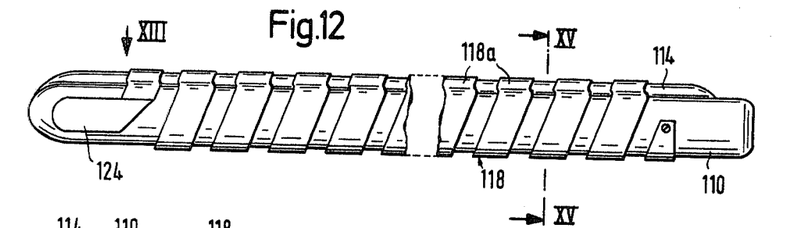
FIG. 12 is a side view of another embodiment of an electro-attachment for a bone nail, for example of FIG. 1.
Figure 13:
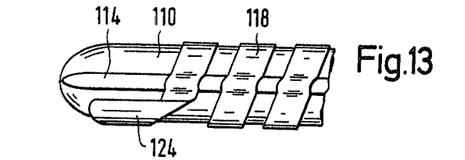
FIG. 13 is an enlarged fragmentary view of the end of the bone nail of FIG. 12 in the region, and looking in the direction of the arrows XIII—XIII of FIG. 12.

If the end of the winding 118 formed by the connection 124 is connected to a bone nail made of metal, then the bone nail acts as a counter electrode, and the voltage difference between the nail 10 (FIG. 1) and the winding portions 118a increase from the connected end of the winding—at the left end of FIG. 12—towards the front end, that is, at the right of FIG. 12. This has the advantage that the largest voltage difference becomes effective at the center and at the distal end of the nail where, from experience, injuries are most likely to occur.

The portions 118a of the winding 118 forming the tissue electrode can be coated with a thin insulating or semiconductive layer. This is true for all the embodiments. The semiconductive or insulating layer controls the voltage effective on the tissue. The voltage can thus be made more uniform, or equalized with respect to the length of the nail, for example by leaving the winding exposed at the region adjacent the connection, or the proximal end of the nail; applying a semiconductive layer in an intermediate range of the winding 118 and applying a thin insulating coating to the distal end, where the voltage is highest. The semiconductive coating can increase in thickness so as to become increasingly insulating towards the distal end.

It is also possible to connect a rectifier, which may be bridged by a resistor between the winding 118 and the bone nail used as an electrode, in order to shift the zero position of the induced a-c, that is, to generate a non-symmetrical a-c, or to provide a-c superimposed on a d-c voltage.

Figure 16:
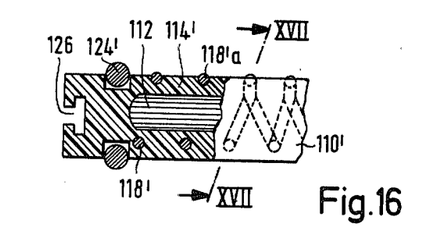
FIG. 16 is a fragmentary longitudinal section of an end portion of an attachment in accordance with another embodiment of the present invention.
Figure 19:
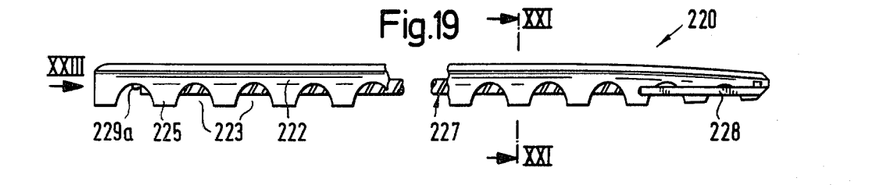
FIG. 19 is a schematic side view of another embodiment of the invention generally shown in FIGS. 2-5.
Figure 20:
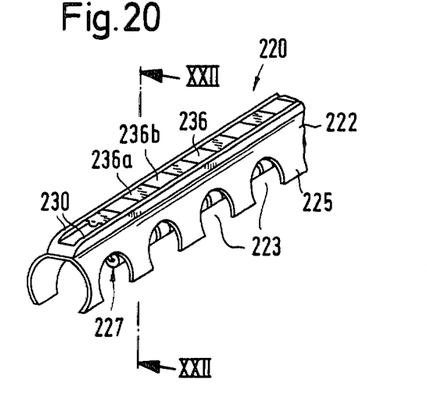
FIG. 20 is a perspective view of the front end of the attachment in accordance with FIG. 19.

Embodiment of FIGS. 16 and 17: The arrangement is similar to that of FIGS. 12 to 15 except that the winding 118' is embedded into an elongated body 110' made of tissue-compatible material, such as PTFE. The arrangement is so made that only the caps or tips 118'a of the windings are exposed at the upper side of the ridge-projection 114' of the body 110'. The body 110' thus serves, simultaneously, as the insulating cover for the major portion of the winding which, in the embodiment of FIGS. 12 to 15, was formed by the foil 122. Thus, the foil 122 may be omitted. The left end of the winding 118'—see FIG. 16—is furnished with a terminal 124', connected in any suitable manner (not shown). The terminal 124' is an outwardly bulged, compressible spring ring. The end of the body 110' is formed with an opening 126 which, for example, is slit-like and has an undercut so that a suitable hook-like tool can be used for easy introduction of the body 110' into a bone nail, and removal from the bone nail, if desired. The conductor 118' has a circular cross section. The tissue electrodes which extend into the projection 114' have a bent needle projection, as best seen in FIG. 17, to fit into the ridge 114'. The cross section of the conductor 118' should be large enough so that the resistance of the conductor is small with respect to that of adjacent tissue so that the shunting short circuit through the tissue will not result in substantial breakdown of the induced voltage.

The body 110 (FIGS. 12 to 15) or 110' (FIGS. 16, 17) can be made quite elastic so that the attachment can be used for bone nails of various types and lengths. Further, the attachment can be made in the form of yard goods ("meter goods") supplied, for example, in strip or coil form, from which the surgeon can cut lengths of desired dimension to fit any given bone nail. A separate connection of the attachment to the bone nail can then be omitted or, if the embodiment of FIGS. 12 to 15 is used, the foil 122 can be foreshortened somewhat, that is made shorter than the winding 118, so that one end of the winding will make contact with the nail. In the embodiment of FIGS. 16, 17, an end of the winding 118' is peeled off from the body 110 and placed around the outside of the body so that, after introduction thereof into the nail, it will engage the inner wall of the nail and make contact therewith. The resilient, compressible material of the body 110 will ensure a good electrical connection.

Embodiment of FIG. 18: The proximal end of the winding 118, or 118', is formed with two springy, reversely extending connecting strips 124a, 124b which engage the inside of the associated bone nail when the attachment is introduced into the bone nail. In all other respects, this embodiment is similar to those of the other embodiments described. The terminal portion 124a, 124b can be supplied as a separate element, with a prong to fit into the body 110 so that, upon removal, the terminal will be removed therewith, and for connection with a stripped-off or non-insulated end portion of the winding 118, 118', respectively, so that the terminal 124a, 124b can be used as a positive connecting terminal with attachment elements supplied in coil or rod form and cut to size, similar to push-type attachments used in the connection of high-tension spark wires in the automotive industry.

Embodiment of FIGS. 19 to 24: The attachment 220 has an elongated body 222 made of biologically tissue-compatible insulating material, such as polyethylene or PTFE. It may, for example, be made of a polyethylene injection-molded part. Its cross section is approximately U or horseshoe-shaped (FIG. 21) and it is furnished with two central longitudinal ribs 230, placed upwardly and in the middle thereof, forming an elongated channel-like groove therebetween in which an electrode arrangement 236 is placed. This embodiment can be used as an attachment, for example, for introduction in the type of nail shown in FIG. 1, which has a continuous longitudinal slot; or for example, with nails which have a rear end which is in form of a closed tube, also known as an AO model. The lateral parts of the body 222 are formed with semicircular cut-outs 223 which increase the flexibility of the body and which are defined laterally by projections 225 acting as spring-like holders which, in use, engage the inner wall of the nail 210 (FIG. 1), and locate and fix the attachment 220 within the nail. The projections 225 can be formed with longitudinal grooves 225a—FIG. 24—to facilitate matching the attachment to nails of different diameters. If nails are used which have a very small diameter, the projections 225 can be trimmed along one or more of the grooves 225a which form break-off or cut-off junctions with the remainder of the body 220.

Figure 21:
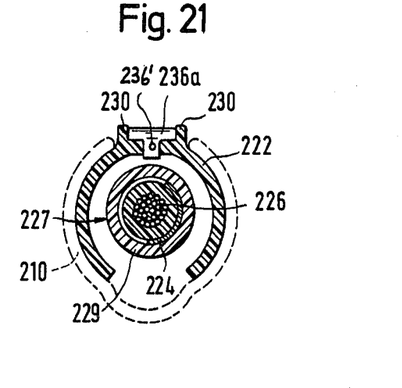
FIG. 21 is a transverse cross section in the plane of XXI—XXI of FIG. 19.
Figure 22:
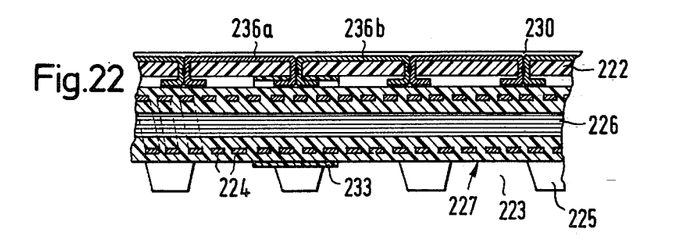
FIG. 22 is an enlarged longitudinal cross section of the forward end of the attachment taken along lines XXII—XXII of FIG. 20.
Figure 23:
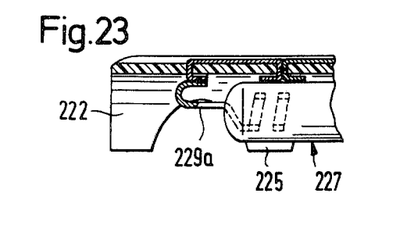
FIG. 23 is an enlarged cross section, similar to FIG. 22, of the front end of the attachment taken along XXIII—XXIII of FIG. 20.
Figure 24:
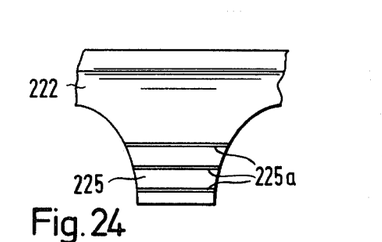
FIG. 24 is a fragmentary side view of another embodiment of the attachment in accordance with FIGS. 19-23.

A receiving coil 227 is located in the space surrounded by the body 222 which includes a coil 224 itself formed, for example, of a single-layer coil of about 60 to 70 windings of a ribbon-type conductor. The coil surrounds a flexible magnetic core 226, formed of a bundle of wires of highly permeable magnetic material, such as mu metal. The receiving coil 224 and the core 226 are surrounded by a biologically compatible plastic 229 and embedded therein. The arrangement 236 comprises a plurality of electrode strips 236a, 236b . . . (FIG. 22), shaped like staples, and connected together at their end face by spot-welding, as schematically indicated by the point 236' in FIG. 21. The legs of the electrode strips 236a, 236b . . . are passed through matching holes formed in the central portion of the body 222, and bent over at the inner ends, as best seen in FIGS. 22 and 23, ensuring reliable and fixed connection between the electrodes 236a . . . with the body 222. The width of the electrode strips essentially conforms to the width of the groove between the longitudinal ribs 230 (FIG. 21).

The coils 227 are secured in the body 222 by short strips of plastic tubing 233 (FIG. 22) held against the body 222 by the bent-over ends of the electrode strips 236a, 236b . . . .

The first winding end 229a of the receiving coil is connected with one end of the electrode arrangement, for example by spot-welding, as seen in FIG. 23.

The other end of the receiving coil is welded to a non-insulated strip of metal 228, made of tissue-compatible material, and secured at the outside of the body 222 to make electrical connection with the nail 210 when the attachment 220 is introduced into the nail. Preferably, two or more strips 228 are provided, bent to respective sides of the body 220.

The length of the attachment 220 may be in the order of, for example, about 22 cm, the distance between the outsides of the longitudinal grooves 230 about 3.5 mm, and so dimensioned that the longitudinal grooves 230 and the electrode arrangement 236 therein fit into the longitudinal slot of the nail 210, while ensuring reliable insulation of the electrode arrangement 236 with respect to the nail. The diameter of the receiving coil arrangement, as coated and as insulated, is about 4 mm, the outer diameter of the receiving coil itself being only slightly less.

Various changes and modifications may be made, and features described in connection with any one of the embodiments may be used with any of the others, within the scope of the inventive concept.

I claim:

1. Electrification attachment for a hollow bone nail formed with a longitudinally extending slot comprising an elongated body (22, 110, 122, 222) of insulating material;
an induction pick-up coil (24, 118, 224) secured on said body;
at least two electrodes (28; 36, 36a, 36b . . . 118a, 236) connected to said coil, at least one of said electrodes being adapted for exposure to the tissue of a patient and secured to said body,
said body and the coil forming an elongated insert being dimensioned to fit within the hollow nail;
a projection (30, 114, 230) formed on the body being dimensioned to fit into the longitudinal slot (12) of the nail,
said at least one of said electrodes being located on said projection and, upon association of the attachment with the bone nail by insertion thereof into the nail, being exposed to the tissue adjacent said bone nail;
said at least one electrode, upon association of the attachment with the bone nail, being electrically insulated with respect to the bone nail;
and means for providing an electrical connecting exposure of at least one other of said electrodes to the tissue of the patient.

2. Attachment according to claim 1, wherein the bone nail is made of electrically conductive material and the means for providing an electrical connecting exposure of said at least one other electrode to the tissue of the patient comprises an electrical connection means making contact with said electrically conductive bone nail.

3. Attachment according to claim 2, wherein said connection means comprises a metallic spring element (28) secured to said body and resiliently, deflectingly engageable with a surface of said bone nail.

4. Attachment according to claim 1, wherein the means for providing an electrical connecting exposure of said at least one other electrode to the tissue of the patient comprises an additional electrode located on said projection for exposure to the tissue adjacent said bone nail.

5. Attachment according to claim 1, wherein the projection (30) comprises an electrode support portion (34), said one electrode being secured to said electrode support portion.

6. Attachment according to claim 1, wherein (FIG. 6) said projection comprises a plurality of electrode support portions (30a, 30b ... 30d);
a plurality of electrodes (36a, 36b ... 36d) secured to respective support portions, said electrodes being connected to different taps of said coil (24).

7. Attachment according to claim 6, wherein said body is formed with severance zones (40a, 40b, 40c) intermediate respective electrode support portions (36a, 36b ... 36d) to permit severing said body into longitudinal elements of different lengths at said severance zones, selectively, in accordance with separation at a respective zone.

8. Attachment according to claim 1, wherein at least a portion (118a, 118'a) of the induction coil is electrically exposed and forms said means for providing an electrical connecting exposure.

9. Attachment according to claim 1, wherein the body (222) is an elongated element of essentially U-shaped or horseshoe-shaped cross section;
the induction coil (224) being positioned within the hollow portion of said body;
said at least one electrode (236) extending longitudinally along the bend of the U, or the root of the horseshoe-shaped body;
and insulating means (230) electrically insulating said at least one electrode with respect to the bone nail (210).

10. Attachment according to claim 9, wherein said insulating means include insulating strips;
and said body is a plastic extrusion or injection molding, said strips being integral with said body.

11. Attachment according to claim 9, wherein said at least one electrode comprises a plurality of electrode portions (236a, 236b ... ) clamped around the outside, through, and the inside of said body in the region of the bend of the U, or at the root of the horseshoe.

12. Attachment according to claim 9, wherein the lateral walls of said body and forming the sides of the U or horseshoe are formed with cut-outs (223) defining projections to increase the flexibility of the elongated body.

13. Attachment according to claim 12, wherein at least some of said projections are formed with break-off or cut-off lines to permit trimming the length of said projections and thus to fit the projections within bone nails of different diameters.

14. Attachment according to claim 1, wherein the coil (24, 118, 224) includes a ferromagnetic core (112, 226) which comprises a plurality of parallel elongated wire-like elements of flexible material.

15. Attachment according to claim 1, wherein said coil (24, 24a, 24b, 118'a) is embedded, at least in part, in said body.

16. Attachment according to claim 1, further including network circuit components secured to said body and comprising a rectifier circuit (FIG. 7: 50, 52, 54, 48; FIG. 8: 50, 52, 54, 62) and connected to said at least two electrodes to supply thereto, upon inductive coupling of the coil with another coil, a d-c voltage on which an a-c voltage is modulated.

17. Attachment according to claim 16, wherein the body is formed with a second projection (66);
further including (FIG. 8) a circuit portion (64) which is part of the rectifier circuit and extending into the second projection (66) of said body to permit severing of the rectifier portion whereby, upon such severing and induction to the coil, the electrode will provide a-c voltage only.

18. Attachment according to claim 16, wherein the at least one electrode has a coating layer which includes at least one material of the group consisting of: semiconductive material and insulating material;
said material being applied to the portion of the electrode adapted to be exposed to the tissue.

* * * * *